US 9,677,983 B2

(12) United States Patent
Spriggs

(10) Patent No.: US 9,677,983 B2
(45) Date of Patent: Jun. 13, 2017

(54) PARTICLE CHARACTERIZATION

(71) Applicant: Malvern Instruments Limited, Malvern, Worcestershire (GB)

(72) Inventor: David Spriggs, Malvern (GB)

(73) Assignee: Malvern Instruments Ltd., Malvern, Worcestershire (GB)

( * ) Notice: Subject to any disclaimer, the term of this patent is extended or adjusted under 35 U.S.C. 154(b) by 66 days.

(21) Appl. No.: 14/957,805

(22) Filed: Dec. 3, 2015

(65) Prior Publication Data

US 2016/0320283 A1    Nov. 3, 2016

(30) Foreign Application Priority Data

May 1, 2015  (EP) .................................... 15166132

(51) Int. Cl.
| | |
|---|---|
| *G01N 1/10* | (2006.01) |
| *G01N 15/02* | (2006.01) |
| *G01N 15/14* | (2006.01) |
| *G01N 21/03* | (2006.01) |
| G01N 15/06 | (2006.01) |

(52) U.S. Cl.
CPC ..... *G01N 15/0211* (2013.01); *G01N 15/1429* (2013.01); *G01N 15/1436* (2013.01); *G01N 21/0303* (2013.01); *G01N 2015/0693* (2013.01)

(58) Field of Classification Search
CPC ...... G01N 21/05; G01N 21/534; G01N 15/06; G01N 2015/0693; G01N 33/2888
USPC ............. 356/246, 72–73, 335–343, 432–440
See application file for complete search history.

(56) References Cited

U.S. PATENT DOCUMENTS

| | | | | |
|---|---|---|---|---|
| 5,305,073 | A | * | 4/1994 | Ford, Jr. ................. G01N 21/49 356/338 |
| 9,279,746 | B2 | * | 3/2016 | Wynn ..................... G01N 21/05 |
| 9,404,849 | B2 | * | 8/2016 | Wynn ..................... G01N 21/05 |
| 2004/0027568 | A1 | | 2/2004 | Maiefski et al. |
| 2010/0110438 | A1 | * | 5/2010 | Furtaw ............... G01N 21/3504 356/437 |

(Continued)

FOREIGN PATENT DOCUMENTS

EP    2 607 883    6/2013

OTHER PUBLICATIONS

Extended European Search Report mailed Oct. 20, 2015, directed to European Application No. 15166132.9; 8 pages.

*Primary Examiner* — Hoa Pham
(74) *Attorney, Agent, or Firm* — Morrison & Foerster LLP

(57) ABSTRACT

A particle characterization apparatus having first and second body parts, a light source, a sample cell and a detector. The light source illuminates dispersed particles within the sample cell with a light beam along an axis to produce scattered light. The sample cell has first and second walls. The walls have internal surfaces arranged to be in contact with the sample and an opposite external surface. The light beam passes through the external surface of the first wall, through the internal surface of the first wall, through the sample, through the internal surface of the second wall, and through the external surface of the second wall. The light source is fixed to the first body part, which engages with the first wall. The detector is fixed to the second body part, which engages with the second wall. The first and second body parts are separable to enable access to the internal surfaces of the walls for cleaning.

20 Claims, 4 Drawing Sheets

(56) References Cited

U.S. PATENT DOCUMENTS

| | | | |
|---|---|---|---|
| 2010/0208269 A1* | 8/2010 | Amano | G01N 15/06 356/442 |
| 2011/0051140 A1* | 3/2011 | Stevens | G01N 21/05 356/436 |
| 2012/0119101 A1* | 5/2012 | Wynn | G01N 21/05 250/373 |
| 2016/0216213 A1* | 7/2016 | O'Brien | G01N 21/09 |
| 2016/0252443 A1* | 9/2016 | Spriggs | G01N 15/1456 356/336 |

* cited by examiner

PARTICLE CHARACTERIZATION

CROSS-REFERENCE TO RELATED APPLICATION

This application claims priority to European Application No. 15166132.9, filed on May 1, 2015, which is incorporated herein by reference in its entirety.

FIELD OF THE INVENTION

The invention relates to a particle characterization instrument, and to a method of characterizing particles.

BACKGROUND OF THE INVENTION

It is known that particles in a sample can be characterized by illuminating the sample and measuring the light scattered by the particles. The particles of the sample are typically dispersed within a sample cell in a dispersant medium during measuring. The dispersant medium is typically air or water, and typically flows through the sample cell during measurement.

The correlation between light scattering and particle characteristics can be described by the well-known Mie solution to Maxwell's equations. Smaller particles tend to result in larger scattering angles, and larger particles result in smaller scattering angles. The light scattered at each of a range of angles from the sample can be used to determine, for example, a size distribution of the particles in the sample. Such a measurement may be referred to as a static light scattering (SLS) measurement.

It is important that the illuminating light beam and scattered light detectors are properly positioned and aligned with each other (along with any other optical elements in the system, such as lenses, mirrors, etc). The light source and detectors may be fixed to a common optical frame, which is housed within (or is part of) the instrument main body.

It is also important for such measurements that the walls of the sample cell are kept clean and are free from scattering centres. If the walls of the sample cell become dirty, they may scatter light, contaminating the signal at the detectors, and resulting in noise, and/or unreliable/inaccurate particle characterization.

Furthermore, it is desirable for the cell walls to be accurately positioned with respect to the illuminating beam and the other components of the instrument (for example any lenses and detector elements). The optical paths are typically designed around a known sample cell position, and may not be able to accommodate a sample cell position that is ill-constrained.

These requirements have previously been addressed by mounting the sample cell on a sample cell sub-assembly which can be removed from the main instrument body. The sample cell windows can subsequently be removed from the sub-assembly for cleaning. Once the sample cell assemblies are cleaned, they can be re-assembled in the sub-assembly, and the sub-assembly returned to the main instrument body.

A clear path is needed within the instrument main body for removing the sample cell sub-assembly. Furthermore, accurate positioning of the sample cell walls with respect to the instrument main body relies on two locating engagements. Firstly, the sub-assembly must accurately locate relative to the instrument main body. Second, the sample cell windows must accurately locate relative to the sample cell sub-assembly. These locating engagements may each be subject to some error, which is undesirable.

An instrument that solves or ameliorates at least some of the above mentioned problems is desired.

SUMMARY OF THE INVENTION

According to the invention, there is provided a particle characterization apparatus comprising: first body part, a second body part, a light source, a sample cell and a detector; wherein:
  the light source is operable to illuminate a sample comprising dispersed particles within the sample cell with a light beam along a light beam axis so as to produce scattered light by interactions of the light beam with the sample;
  the detector is configured to detect the scattered light;
  the sample cell comprises a first wall and a second wall, each of the first wall and second wall comprising an internal surface arranged to be in contact with the sample and an opposite external surface, the first and second wall being arranged so that the light beam axis passes through the external surface of the first wall, then through the internal surface of the first wall, then through the sample, then through the internal surface of the second wall, then through the external surface of the second wall;
  the light source is fixed to the first body part and the first body part is configured to engage with the first wall;
  the detector is fixed to the second body part and the second body part is configured to engage with the second wall;
  the first body part is separable from the second body part to enable access to the internal surface of each of the first wall and second wall for cleaning.

The first and second body parts may prevent access to the internal surfaces of the first and second wall when the first and second body part are not separate (i.e. when the first and second body part are assembled).

The detector may be configured to provide an output that is suitable for determining a particle size distribution within the sample. The particle characterization apparatus may comprise a processor that is configured to determine from the detector output a particle size distribution within the sample.

The apparatus may comprise an instrument main body that is configured to split (from an assembled state) into the first body part and second body part.

The first and second wall of the sample cell may be separable. The main body and sample cell may be configured such that splitting the main body results in separation of the first and second wall.

The apparatus may be configured such that the first and second body parts can be separated without detaching the light source from the first body part, and without detaching the detector from the second body part.

The first and/or second wall may comprise a plano-convex lens, the respective external surface being a convex surface of the lens and the respective internal surface being a planar surface of the lens.

The first body part may comprise a first mount that directly engages with the first wall.

The second body part may comprise a second mount that directly engages with the second wall.

The first mount and/or the second mount may engage only with the external surface of the respective first and/or second wall.

The first mount and/or the second mount may be configured to have only three points of engagement with the external surface of the respective first and/or second wall.

The first mount and/or second mount may be configured to engage with the respective first and/or second wall only via spherical bearing surfaces of the respective mount.

The first body part and second body part may together further comprise a third mount, by which the first body part may be engaged with the second body part in a kinematically determinant manner.

The apparatus may comprise a first base portion for standing the assembled apparatus on a planar surface with the first light beam axis substantially normal to the planar support surface.

One of the first body part and the second body part may comprise the first base portion. The other of the first body part and the second body part may comprise a second base portion for standing the respective body part on a planar surface when the first body part is separated from the second body part.

The particle characterization apparatus may further comprise a seal element, configured to engage with the internal surfaces of the first and second walls when the first body part is engaged with the second body part, to contain the sample between the first and second walls.

The external surface of the first and/or second wall may be spherical.

The external surface of each of the first and second wall may be spherical. The centre of curvature of the respective external surfaces of the first and second walls may be offset when the apparatus is assembled with the first wall engaged by the first body part, the second wall engaged by the second body part, and the first body part engaged with the second body part.

The particle characterization apparatus may comprise a first housing part attached to the first body part, the first housing part containing the light source, and a second housing part attached to the second body part, the second housing part containing the detector.

BRIEF DESCRIPTION OF THE DRAWINGS

Examples embodiments will be described, purely by way of example, with reference to the accompanying drawings, in which.

DETAILED DESCRIPTION OF THE INVENTION

Figure 1:
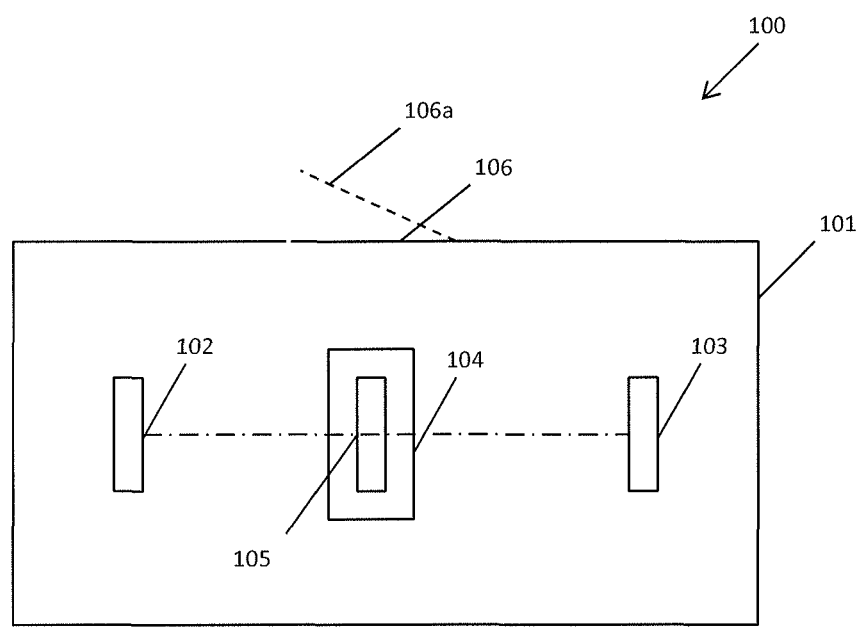
FIG. 1 is a schematic of an existing instrument with a unitary body.

FIG. 1 shows a prior art particle characterization apparatus 100, comprising a body 101, to which is attached a light source 102 and detector 103. The body 101 further supports a sample holder sub-assembly 104 that in turn supports a sample cell 105. The light source 102 produces a light beam that illuminates the sample cell 105 along a light beam axis.

The light source 102 and detector 103 are arranged in a predetermined position and orientation relative to the sample cell 105, so that dispersed particles in a sample within the sample cell may be characterised based on scattered light incident on the detector 103.

The body 101 comprises a housing that contains the light source 102, detector 103 and sample cell 105. The sample holder sub-assembly 104 can be removed for cleaning of the sample cell 105 by opening a door 106 in the body housing. The sample cell 105 can be removed from the sub-assembly 104, cleaned, and then returned.

Figure 2:
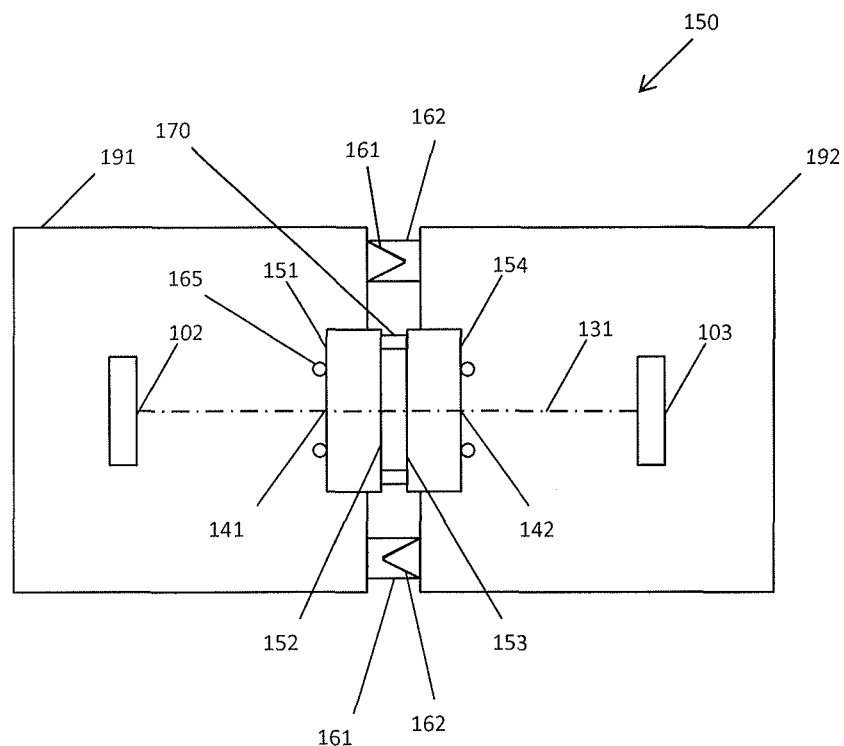
FIG. 2 is a schematic of an embodiment with flat sample cell walls, with the first body part separated from the second body part by a short distance.
Figure 3:
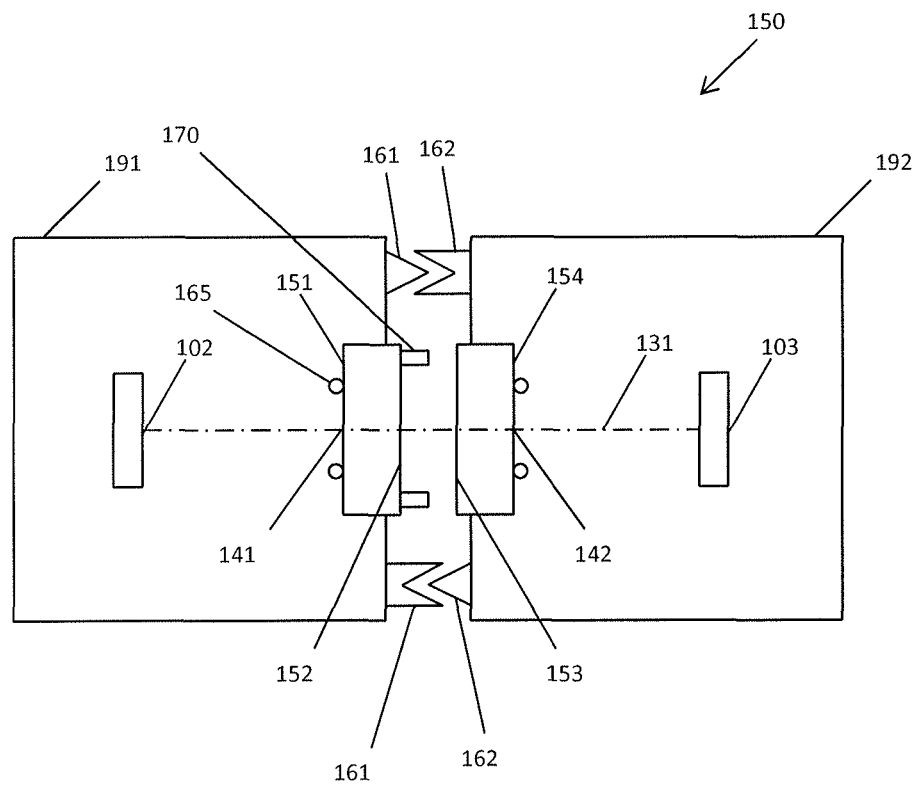
FIG. 3 is a schematic of the embodiment of FIG. 2 in an assembled state.

FIGS. 2 and 3 show particle characterization apparatus 150 according to an embodiment. The apparatus 150 comprises a first body part 191, second body part 192, light source 102, sample cell, and detector 103. The sample cell comprises a first wall 141, second wall 142 and seal 170. The first and second body parts 191 may together comprise the instrument main body.

In contrast to the prior art, the body of the apparatus 150 is split into two separable parts. FIG. 3 shows the apparatus 150 with the first and second body part 191, 192 separated by short distance, and FIG. 2 shows the apparatus 150 assembled. The first body part 191 supports the first wall 141 of the sample cell, and the second body part 192 supports the second wall 142 of the sample cell. The light source 102 is fixed to the first body part 191, and the detector 103 is fixed to the second body part 192.

The first body part 191 and second body part 192 comprise a mount 161, 162, by which the first and second body part may be assembled together in a kinematically determinant manner, with a defined orientation and position in all 6 degrees of freedom. When the first and second body part 191, 192 are assembled in this way, the light source 102 and the detector 103 are properly aligned and positioned with respect to each other. The light source 102 is operable to produce a light beam for illuminating a sample within the sample cell along a light beam axis 131. The light beam axis 131 is precisely aligned with respect to the detector 103 by the mutual alignment of the first and second body parts 191, 192.

The first body part 191 supports the first wall 141 of the sample cell on a first mount. The first mount in this embodiment comprises three spherical elements 165 (two of which are shown in FIGS. 2 and 3). The first mount engages with the external surface 151 of the first wall 141, so as to constrain the orientation and position of the first wall 141 with respect to the first body part 191 (and in turn the light source 102 and detector 103).

A clip or other similar retaining means may be provided for retaining the first wall 141 engaged with the first mount, for instance when the first and second body parts are separated. A similar retaining means may be provided for retaining the second wall 142 engaged with the second mount.

The second body part 192 supports the second wall 142 of the sample cell on a second mount. The second mount in this embodiment comprises three spherical elements 165 (two of which are shown in FIGS. 2 and 3). The second mount engages with the external surface 154 of the second wall 142, so as to constrain the orientation and position of the second wall 142 with respect to the first body part 191 (and in turn the light source 102 and detector 103).

The spherical elements 165 of the first and/or second mount may conveniently be spherical bearings (which are both hard and precisely shaped and therefore well suited to constraining the sample cell walls 141, 142).

The first and/or second mount may alternatively comprise an annular shoulder against which the respective first and/or second wall 141, 142 engages, or may comprise any other suitable mechanical support.

When the apparatus 150 is assembled (as shown in FIG. 2) the seal 170 engages with the interior surface 152 of the first wall 141 and with the interior surface 153 of the second wall 142, so that a sample may be contained and/or flow through the sample cell. The sample cell is disassembled when the first 191 and second body parts 192 are separated, because this results in the seal 170 disengaging from at least one of the sample cell walls 141, 142.

The first and second sample cell walls 141, 142 may each be clamped against their respective mounts by clamping means. Alternatively, the seal 170 may be resiliently deformable, and may be used to urge each of the first and second walls 141, 142 into engagement with their respective mount when the first and second body parts 191, 192 are assembled. The first and second mount may engage only with the respective external surfaces 151, 154 of the first and second wall 141, 142.

When the first and second body part 191, 192 are assembled, the light beam axis 131 passes through the external surface 151 of the first wall 141, then through the internal surface 152 of the first wall 141, then through the sample (contained by the seal 170), then through the internal surface 153 of the second wall 142, then through the external surface 154 of the second wall 142.

Since the first and second body parts 191, 192 are separable, access to the internal surfaces 152, 153 of the sample cell for cleaning can be obtained without removing the first and second sample cell walls 141, 142 from their respective mounts. This minimises the potential for disturbing the alignment of the sample cell as a result of cleaning the sample cell walls 141, 142. Only one mount (between the first and second body parts 191, 192) need be disturbed, which is in contrast to the prior art, where the mounting between the sample cell and sub-assembly is disturbed as well as the mounting between the sub-assembly and the main body.

A further advantage of the separable body parts 191, 192 is that the instrument may be made more dust-proof, because there is no need for a door (106 in FIG. 1) for removing the sample cell from. The first housing and/or the second housing may be made dust proof. The first housing and/or second housing may comprise a dust proof enclosure that is configured to prevent ingress of dust to an interior of the respective housing. A window in the dust proof enclosure may be provided for the light beam to pass through to or from the sample cell. Alternatively, to avoid reflections and optical scattering in such a window, the first wall 141 may complete a dust proof enclosure of the first housing and/or the second wall 142 may complete a dust proof enclosure of the second housing, when the apparatus 150 is assembled. A first compliant seal member may be provided as part of the first mount, that provides a dust proof seal between the external surface 151 of the first wall 141 and the first mount. A second compliant seal member may be provided as part of the second mount, that provides a dust proof seal between the external surface 154 of the second wall 142 and the first mount. The first and/or second compliant seal member may be at least 10 times as compliant as the bearing surfaces of the respective first and/or second mount that constrain the orientation and position of the first and second walls 141, 142 when the apparatus 150 is assembled.

With such an arrangement, in normal usage a user of the apparatus may have no reason to disturb the dust proof enclosures, so the interior of the apparatus will remain free from contamination. The first and second wall 141, 142 may be cleaned without disengaging them from their respective first and second mounts.

A particle characterization apparatus 150 may include a base portion, on which the apparatus is intended to stand, in use. The base portion may be for resting on a planar surface (such as a bench-top). Typically, the light beam axis 131 in a particle characterization apparatus (through the sample cell) is parallel to the bench-top. With a split-body instrument according to an embodiment, it may be convenient for the system to stand with the light beam axis 131 substantially normal to the bench-top (or other planar support surface).

Figure 4:
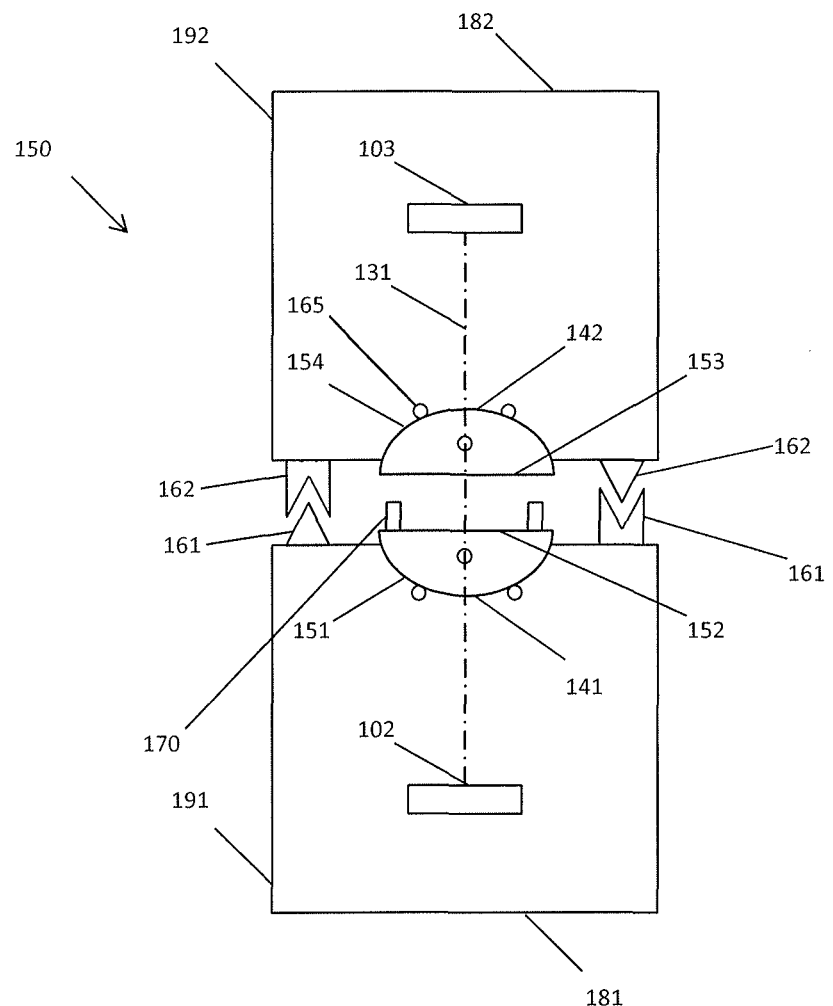
FIG. 4 is a schematic of an embodiment with planoconvex sample cell walls, with the first body part separated from the second body part by a short distance.
Figure 5:
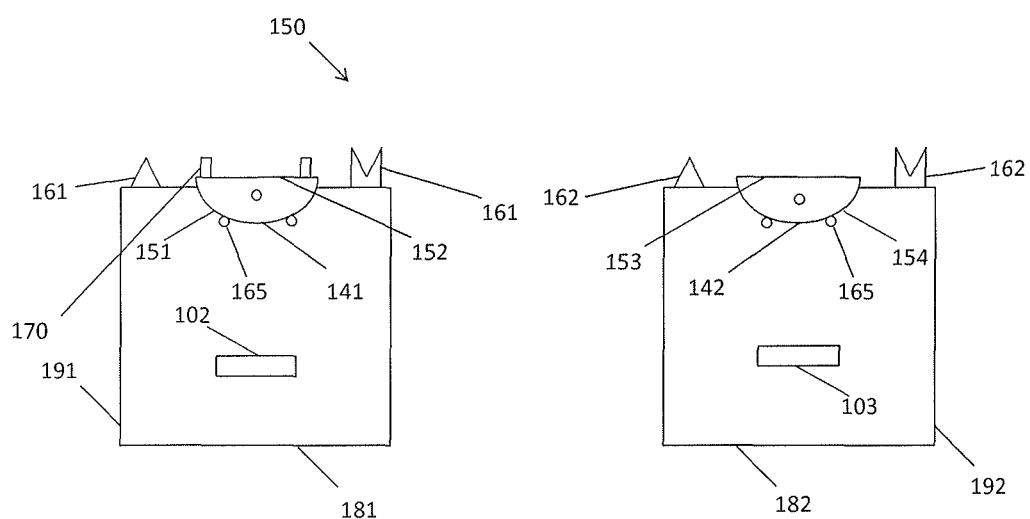
FIG. 5 is a schematic of the embodiment of FIG. 4 in a disassembled state, suitable for cleaning.

FIGS. 4 and 5 show a particle characterization apparatus 150 that may include any of the features described with reference to FIGS. 2 and 3. In this embodiment the first and second sample cell wall 141, 142 each comprise a planoconvex lens. The external surface 151, 154 of each of the first and second wall 141, 142 is convex (e.g. spherical), and the internal surface 152, 153 of each of the first and second wall 141, 142 is planar.

An effect of the curved external surfaces 151, 154 of the sample cell walls 141, 142 is to allow light scattered at higher angles to escape, with less refraction at the sample cell/air interface. Flat external surfaces result in spreading out of scattered light as it is refracted at the sample cell wall/air interface, and a critical angle exists at which scattered light is totally internally reflected. The use of a sample cell with a convex external surface 151 or 154 enables a broader range of scattering angles to be detected, increases the amount of scattered light per steradian outside the sample cell (because scattered light is not spread by refraction at the sample cell/air interface) and reduces optical noise (because any totally internally reflected scattered light ends up as optical noise).

These advantages enable an instrument with reduced size that has similar performance to larger existing instruments with flat sample cell walls. The sample cell walls in such an arrangement tend to have a larger volume than conventional flat sample cell walls, due to their shape. The potential for a reduced size apparatus employing a lensed sample cell increases the problems associated with a conventional sample cell sub-assembly. A suitable sub-assembly would be large relative to the main body of the instrument. Providing the necessary clear space for such a sub-assembly to be removable would tend to increase the total size of the apparatus, negating at least some of the potential advantages of a lensed sample cell. There is therefore a synergy between lensed sampled cells and a split body apparatus.

The first mount may comprise three contact points, that engage only with the exterior surface 151 of the first wall 141. Similarly, the second mount may comprise three contact points, that engage only with the exterior surface 154 of the second wall 142. If the external surfaces 151, 154 are spherical, this three point engagement will constrain the position of the centre of curvature of the external surface 151, 154 relative to the respective body part 191, 192, and the first and second wall 141, 142 may rotate only about this respective centre of curvature while engaged with the contact points.

When apparatus 150 is assembled and the first and second body parts 191, 192 are engaged with each other, the centre of curvature of the first wall 141 and the second wall 142 are in different positions (i.e. are offset from each other). The seal 170 is also engaged with the internal surfaces 152, 153, which constrains these surfaces to be mutually parallel. This means that any rotation of the first wall 141 must be shared by the second wall 142. However, the first and second walls 141, 142 may only rotate about their respective centres of curvature, which are in different positions. The net result is that the first and second walls 141, 142 are fully constrained by their respective engagement with the first and second mount, and their mutual engagement via the seal 170.

In the embodiment of FIGS. 4 and 5, the first body part 191 comprises a first base portion 181 for standing the assembled apparatus 150 (or just the first body part 191) on a planar surface (such as a bench top), with the first light beam axis 131 substantially normal to the planar surface. Substantially normal may mean within 30 degrees of normal. The second body part 192 comprises a second base portion 182.

Referring to FIG. 5, when the apparatus 150 is split, the first and second body parts 191, 192, may each stand on their respective base portion 181, 182, with the first wall 141 retained against the first mount by gravity, and the second wall retained against the second mount by gravity. This may improve the ease with which the inner surfaces 152, 153 of the cell walls may be cleaned, because no clamping means are required to keep the cell walls in place during cleaning.

Although the detector in the example embodiments are represented by a rectangle, it will be understood that the detector may comprise a plurality of light sensitive elements, each element arranged to detect light at a different range of scattering angles. The detectors therefore provides information about the scattered light intensity as a function of scattering angle, which can be used to calculate the size distribution of particles within the sample (e.g. by Mie scattering theory). The detector may comprise a focal plane array for detecting small angle scattering. The detector may also comprise a plurality of separate detectors, for example for detecting light scattered at relatively large angles (e.g. >30 degrees).

The instrument may further comprise backscatter detectors that are within the first body part.

Although specific examples have been described, these are not intended to be limiting, and the skilled person will understand that further variations are possible, within the scope of the invention, which is defined by the appended claims.

The invention claimed is:

1. A particle characterization apparatus comprising:
    first body part, a second body part, a light source, a sample cell and a detector; wherein:
        the light source is operable to illuminate a sample comprising dispersed particles within the sample cell with a light beam along a light beam axis so as to produce scattered light by interactions of the light beam with the sample;
        the sample cell comprises a first wall and a second wall, each of the first wall and second wall comprising an internal surface arranged to be in contact with the sample and an opposite external surface, the first and second wall being arranged so that the light beam axis passes through the external surface of the first wall, then through the internal surface of the first wall, then through the sample, then through the internal surface of the second wall, then through the external surface of the second wall;
        the light source is fixed to the first body part and the first body part is configured to engage with the first wall;
        the detector is fixed to the second body part and the second body part is configured to engage with the second wall;
        the first body part is separable from the second body part to enable access to the internal surface of each of the first wall and second wall for cleaning.

2. The particle characterization apparatus of claim 1, wherein the detector is configured to provide an output that is suitable for determining a particle size distribution.

3. The particle characterization apparatus of claim 2, wherein the detector comprises a plurality of detectors, each arranged to receive light scattered at a different range of scattering angles.

4. The particle characterization apparatus of claim 1, wherein the apparatus comprises an instrument main body that is configured to split into the first body part and the second body part.

5. The particle characterization apparatus of claim 1, wherein the first and second wall of the sample cell are separable.

6. The particle characterization apparatus of claim 1, wherein the first and second body parts can be separated without detaching the light source from the first body part, and without detaching the detector from the second body part.

7. The particle characterization apparatus of claim 1, wherein the first and/or second wall comprise a planoconvex lens, the respective external surface being a convex surface of the lens and the respective internal surface being a planar surface of the lens.

8. The particle characterization apparatus of claim 1 wherein the first body part comprises a first mount that directly engages with the first wall.

9. The particle characterization apparatus of claim 1 wherein the second body part comprises a second mount that directly engages with the second wall.

10. The particle characterization apparatus of claim 1 wherein the first mount and/or the second mount engages only with the external surface of the respective first and/or second wall.

11. The particle characterization apparatus of claim 1, wherein the first mount and/or the second mount is configured to have only three points of engagement with the external surface of the respective first and/or second wall.

12. The particle characterization apparatus of claim 1, wherein the first mount and/or second mount are configured to engage with the respective first and/or second wall only via spherical bearing surfaces of the respective mount.

13. The particle characterization apparatus of claim 1, wherein the first body part and second body part together further comprise a third mount, by which the first body part is engageable with the second body part in a kinematically determinant manner.

14. The particle characterization apparatus of claim 1, wherein the apparatus comprises a first base portion for standing the assembled apparatus on a planar surface with the first light beam axis substantially normal to the planar support surface.

15. The particle characterization apparatus of claim 1, wherein one of the first body part and the second body part comprises the first base portion, and the other of the first body part and the second body part comprises a second base portion for standing the respective body part on a planar surface when the first body part is separated from the second body part.

16. The particle characterization apparatus of claim 1, further comprising a seal element, configured to engage with the internal surfaces of the first and second walls when the first body part is engaged with the second body part, to contain sample between the first and second walls.

17. The particle characterization apparatus of claim 1, wherein the external surface of the first and/or second wall are spherical.

18. The particle characterization apparatus of claim 1, wherein the external surface of each of the first and second wall are spherical, and the centre of curvature of the respective external surfaces of the first and second walls are offset when the apparatus is assembled with the first wall engaged by the first body part, the second wall engaged by the second body part, and the first body part engaged with the second body part.

19. The particle characterization apparatus of claim 1, further comprising a first housing part attached to the first body part, the first housing containing the light source, and a second housing part attached to the second body part, the second housing part containing the detector.

20. The particle characterization apparatus of claim 1, wherein the first housing and first wall form a dust proof enclosure when the first wall is engaged with the first body part, and/or the second housing and second wall form a dust proof enclosure when the second wall is engaged with the second body part.

* * * * *